(12) United States Patent
Pendlebury

(10) Patent No.: US 8,992,473 B2
(45) Date of Patent: Mar. 31, 2015

(54) STEM CELL DELIVERY DEVICE FOR ORTHOBIOLOGICS APPLICATIONS

(75) Inventor: Robert Pendlebury, Hollymount (IE)

(73) Assignee: National University of Ireland, Galway, Galway (IE)

( * ) Notice: Subject to any disclaimer, the term of this patent is extended or adjusted under 35 U.S.C. 154(b) by 234 days.

(21) Appl. No.: 13/378,290

(22) PCT Filed: Jun. 14, 2010

(86) PCT No.: PCT/EP2010/003542
§ 371 (c)(1),
(2), (4) Date: Dec. 14, 2011

(87) PCT Pub. No.: WO2010/145786
PCT Pub. Date: Dec. 23, 2010

(65) Prior Publication Data
US 2012/0095441 A1 Apr. 19, 2012

Related U.S. Application Data

(60) Provisional application No. 61/187,013, filed on Jun. 15, 2009.

(51) Int. Cl.
*A61F 7/12* (2006.01)
*A61M 5/44* (2006.01)
*A61M 5/28* (2006.01)
*A61M 5/32* (2006.01)

(52) U.S. Cl.
CPC ............... *A61M 5/445* (2013.01); *A61M 5/282* (2013.01); *A61M 5/3298* (2013.01); *A61M 2205/3653* (2013.01); *A61M 2205/8206* (2013.01)
USPC ............ 604/113; 604/114; 604/291; 604/522

(58) Field of Classification Search
CPC ....... A61M 5/44; A61M 5/445; A61M 1/025; A61M 2205/8206
USPC .................. 604/290, 291, 506, 522, 113, 114
See application file for complete search history.

(56) References Cited

U.S. PATENT DOCUMENTS

| | | | | |
|---|---|---|---|---|
| 5,243,833 | A * | 9/1993 | Coelho et al. | 62/376 |
| 5,520,885 | A * | 5/1996 | Coelho et al. | 422/527 |
| 5,733,263 | A * | 3/1998 | Wheatman | 604/141 |
| 6,726,654 | B2 * | 4/2004 | Rosenman | 604/113 |
| 7,011,797 | B2 * | 3/2006 | Bakke | 422/307 |
| 7,722,839 | B2 * | 5/2010 | Kuzyk | 422/307 |
| 8,012,416 | B2 * | 9/2011 | Kuzyk | 422/38 |
| 8,028,532 | B2 * | 10/2011 | Voute et al. | 62/66 |
| 2003/0082069 | A1 * | 5/2003 | Kuzyk | 422/1 |
| 2003/0114795 | A1 * | 6/2003 | Faries et al. | 604/113 |
| 2005/0136161 | A1 * | 6/2005 | Okita | 426/393 |

(Continued)

*Primary Examiner* — Nicholas Lucchesi
*Assistant Examiner* — Gerald Landry, II
(74) *Attorney, Agent, or Firm* — Schiff Hardin LLP

(57) ABSTRACT

A method and apparatus for thawing and delivery of cryogenically frozen biological material, such as stem cells includes a housing for receiving a pouch of frozen cells, a heating element against which the pouch is placed for applying defrosting heat to the pouch, and a squeezing apparatus for applying a squeezing force to the pouch after or upon thawing of the cells. The squeezing force may be applied by a roller pressing the pouch against the heating element, which forces the thawed cells from a needle or tube connected to the housing and/or to the pouch. A rechargeable battery in the housing supplies power to the heating element and the squeezing apparatus.

8 Claims, 7 Drawing Sheets

(56) References Cited

U.S. PATENT DOCUMENTS

| | | | |
|---|---|---|---|
| 2006/0032607 A1* | 2/2006 | Wisniewski | 165/47 |
| 2006/0236703 A1* | 10/2006 | Rada | 62/62 |
| 2007/0127901 A1* | 6/2007 | Kuzyk | 392/446 |
| 2007/0270744 A1* | 11/2007 | Dacquay et al. | 604/114 |
| 2008/0161753 A1* | 7/2008 | Gillespie et al. | 604/65 |
| 2009/0118684 A1* | 5/2009 | Da Silva et al. | 604/290 |
| 2009/0204071 A1* | 8/2009 | Grant et al. | 604/113 |

\* cited by examiner

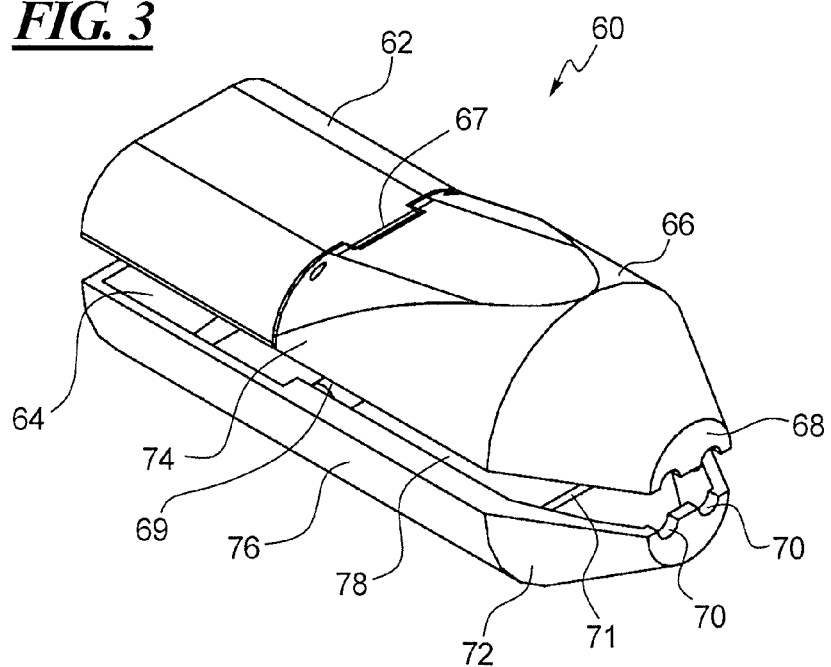
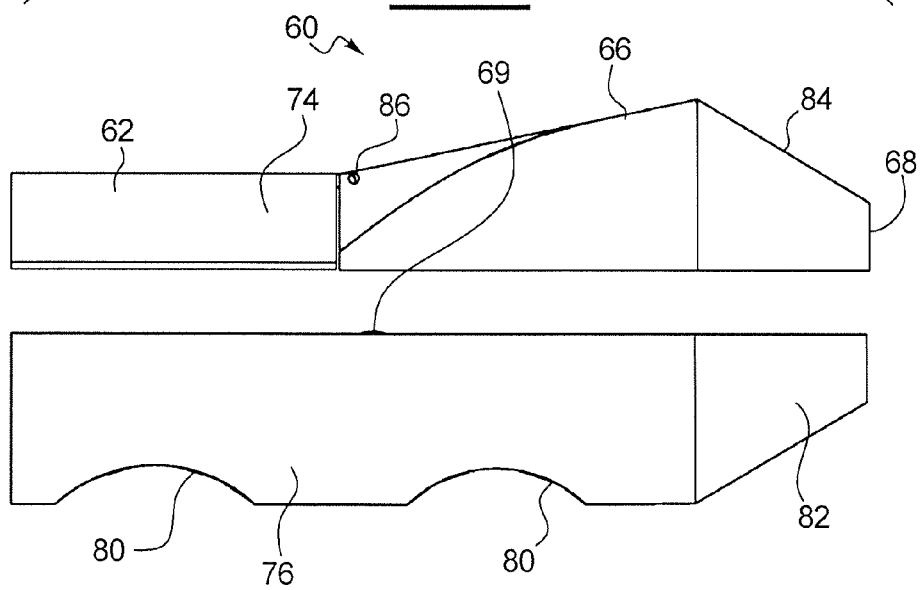

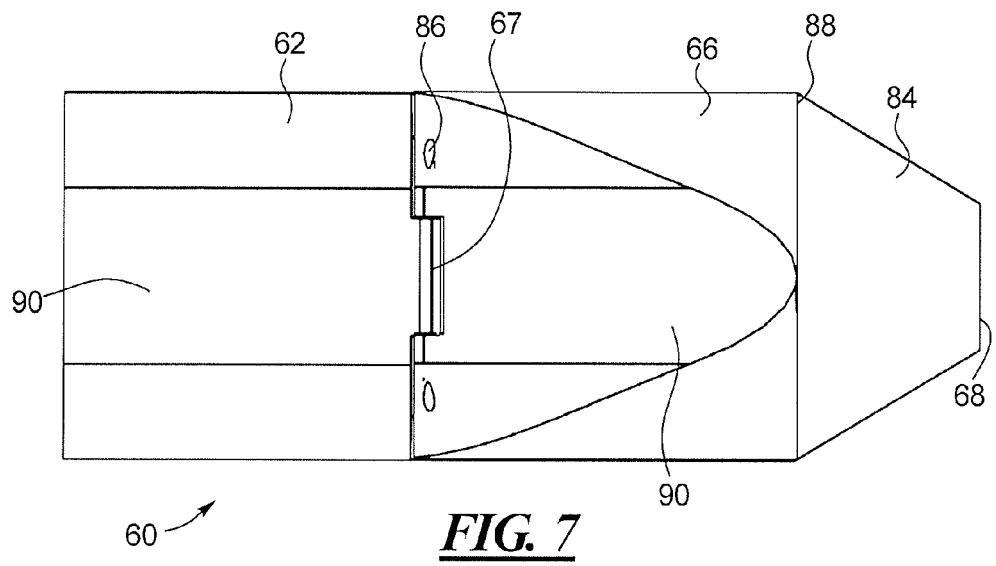
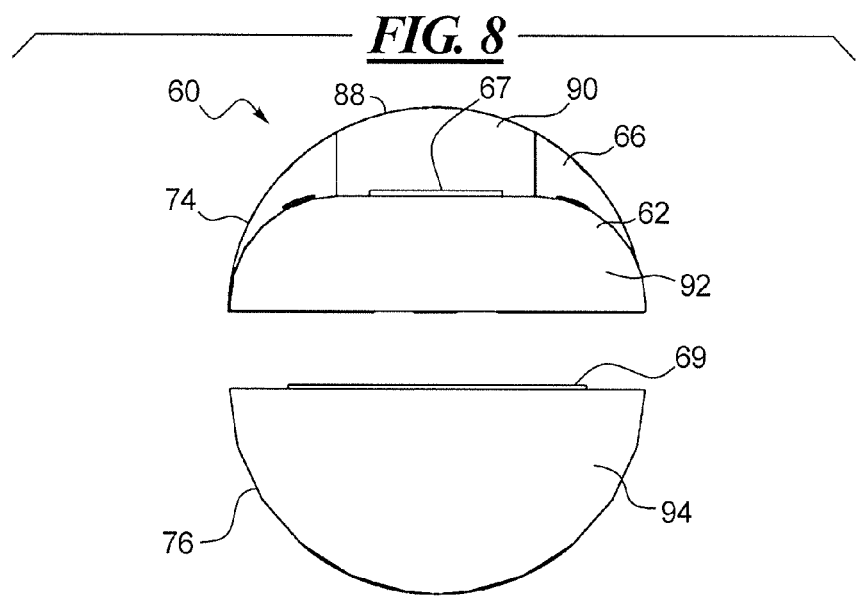

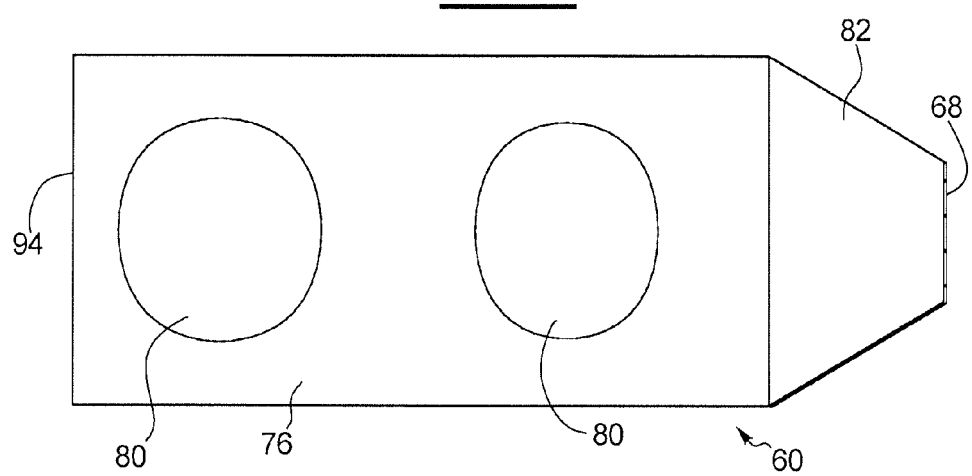
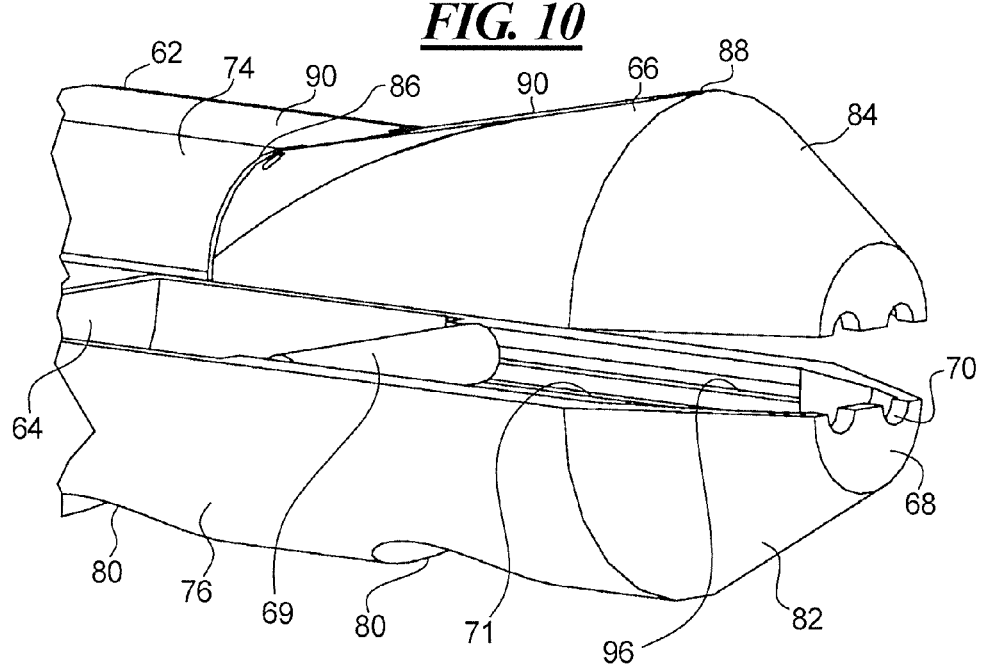

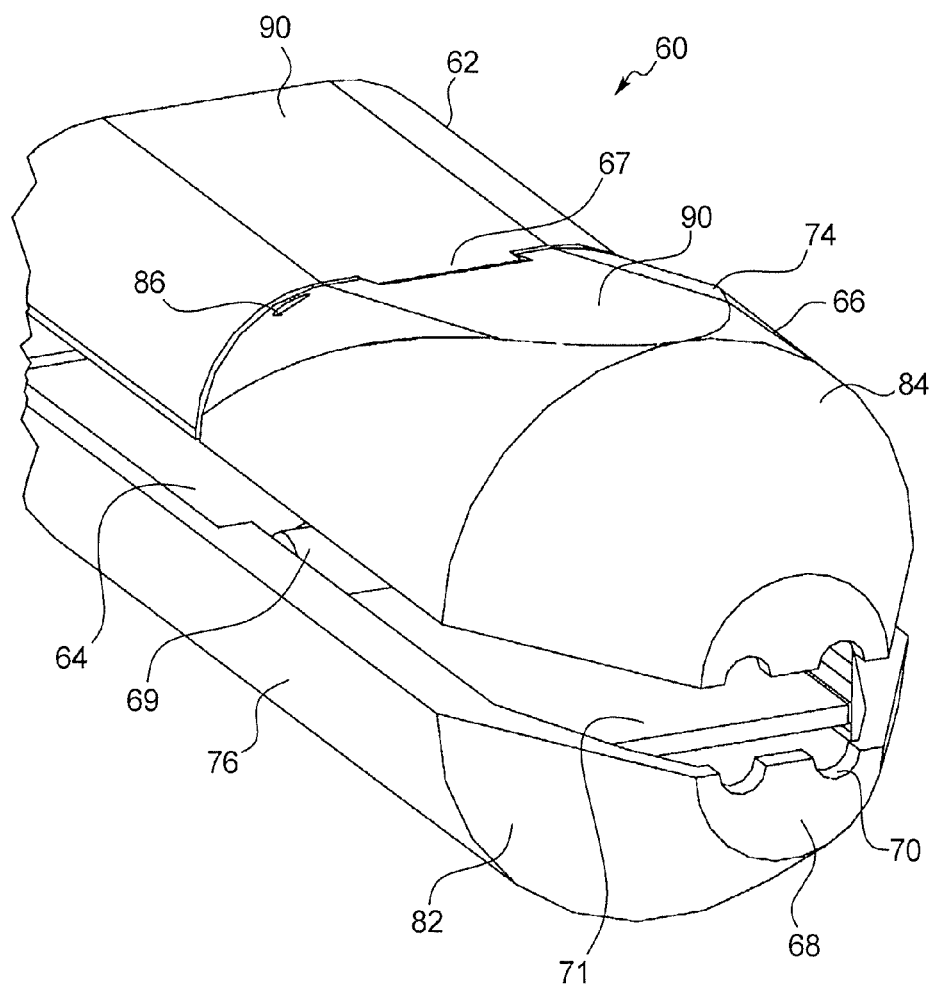

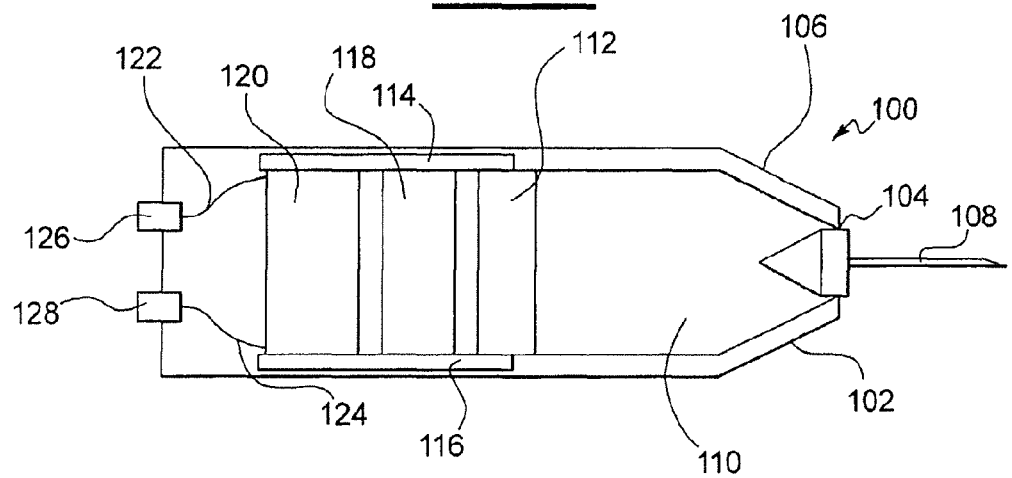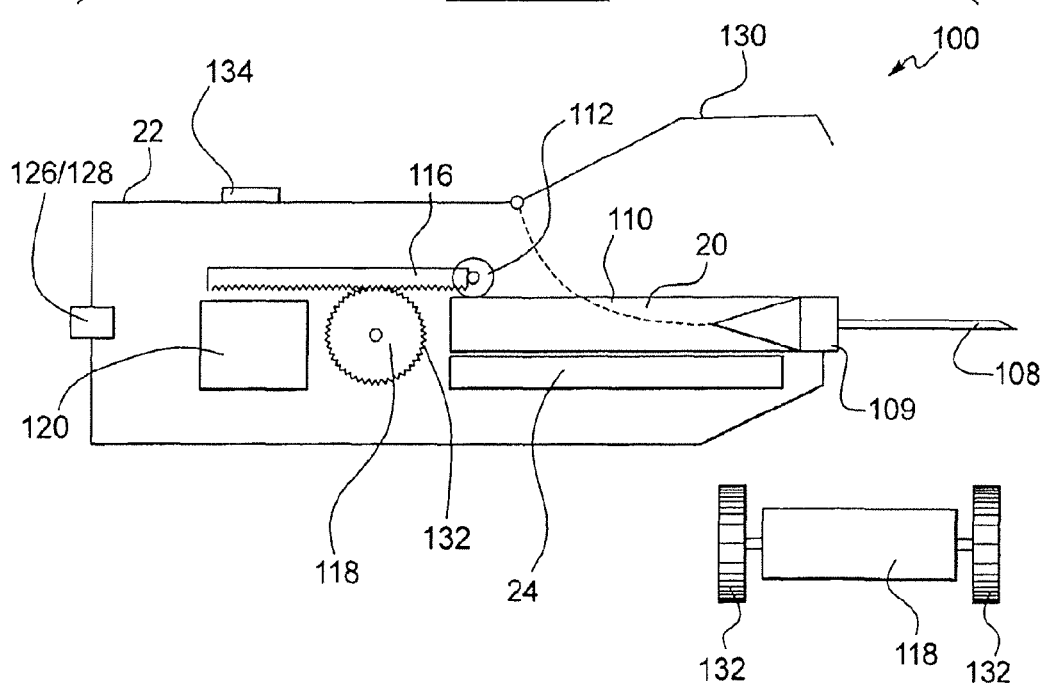

STEM CELL DELIVERY DEVICE FOR ORTHOBIOLOGICS APPLICATIONS

CROSS-REFERENCE TO RELATED APPLICATION

This application claims the benefit of U.S. Provisional Patent Application Ser. No. 61/187,013, filed Jun. 15, 2009, which is incorporated by reference herein.

BACKGROUND OF THE INVENTION

1. Field of the Invention

The present invention relates generally to a device and method for warming frozen cells and other biological materials and in particular to a delivery device and method for thawing and squeezing pouches of frozen cells.

2. Description of the Related Art

Stem cells are cells which are capable of differentiating into other cells depending upon their environments. For example, hematopoietic cells transform into cells found in blood and bone marrow, endolethial stem cells transform into cells associated with the vascular system, such as veins and arteries, while mesenchymal stem cells form bone, cartilage, muscle and fat. These cells are generally stored in a cryogenically frozen condition. In order to use these cells in a clinical environment, they have to be defrosted or thawed. Defrosting or thawing must be performed using a particular thermal profile to avoid damage to the cells by the formation of ice crystals. This generally requires that the defrosting of the cells take place in a thawing apparatus to control the temperature profile. In one example, the thawing of the stem cells prior to injection is usually done in a water bath which is set at a temperature of 37 degrees C. and takes around 3-4 minutes for a 5 ml vial. For pouches of frozen cells, prior solutions involve thawing out the pouches of stem cells in a water bath, set at a temperature of 37 C, for about 5 minutes. After the cells are thawed, the defrosted cells are placed in a device suitable for the delivery of the cells to the target site. For vascular applications, the incorporation of stem cells onto stents has been described but for orthopaedic treatments, the stem cells are typically injected using standard arthroscopic procedures.

SUMMARY OF THE INVENTION

The present device and method solves the problem of how to inject stem cells into the body without having to thaw the cells first in an external apparatus and then transfer them to a delivery device. A delivery device is provided that includes a warming element to apply heat to a container of frozen cells and includes an apparatus to apply a force to the container to deliver the cells as they are thawed. In particular, a pouch containing frozen stem cells is placed into the delivery device in thermal contact with a heating element that is mounted within the delivery device. A conduit, tube, needle or other carrier device is connected to the pouch, or is already provided on the pouch. The heating element is operated to heat the pouch according to a thawing profile to thereby thaw the frozen cells. A squeezing apparatus is provided in the delivery device to squeeze the pouch and deliver the thawed cells through the conduit, tube, needle or other carrier device. The frozen cells are both thawed and delivered by the same device so that the use of ancillary equipment is not required to thaw out the stem cells for delivery.

BRIEF DESCRIPTION OF THE DRAWINGS

FIG. 3 is a top perspective view of a stem cell delivery device according to the principles of the present invention, shown with the two halves of the device separated for purposes of illustration;

FIG. 4 is a side elevational view of the stem cell delivery device of FIG. 3, shown with the two halves separated for purposes of illustration;

FIG. 7 is a top plan view of the stem cell delivery device;

FIG. 8 is an end elevational view of the stem cell delivery device from the opposite end as compared to FIG. 5, shown with the two halves of the device separated;

FIG. 9 is a bottom plan view of the stem cell delivery device;

FIG. 10 is an enlarged front perspective view of the open stem cell delivery device showing the interior of the device;

FIG. 11 is an enlarged end perspective view of the stem cell delivery device;

FIG. 12 is a plan view of the interior of the delivery device to which is attached a delivery needle; and FIG. 13 is a side cross sectional view of the delivery device to which is attached a delivery needle and within which is a pouch of frozen stem cells.

DETAILED DESCRIPTION OF THE PREFERRED EMBODIMENTS

When manufactured or prepared, stem cells and other biological materials are placed into containers suitable for cryogenic storage. One such container is a pouch, much like pouches used for storing blood and other types of body fluids and cells. The pouches of stem cells are stored in a cryogenically frozen condition until they are needed. When removed from cryogenic storage, the pouch 20 as shown in FIG. 13 is placed directly into a delivery device 22 and in contact with a heating element 24 in the delivery device 22. The heating element 24 of a preferred embodiment is a thermoelectric device (TED). The thermoelectric device is activated to thaw the frozen cells in the pouch 20. A TED 24 is used instead of a standard resistance heater because the thermal output is regulated depending upon the temperature of the medium which it is trying to heat up. Consequently, as the stem cells warm up the thermal output of the TED reduces so as not to damage the stem cells, particularly those close to the walls of the pouch.

Figure 1:
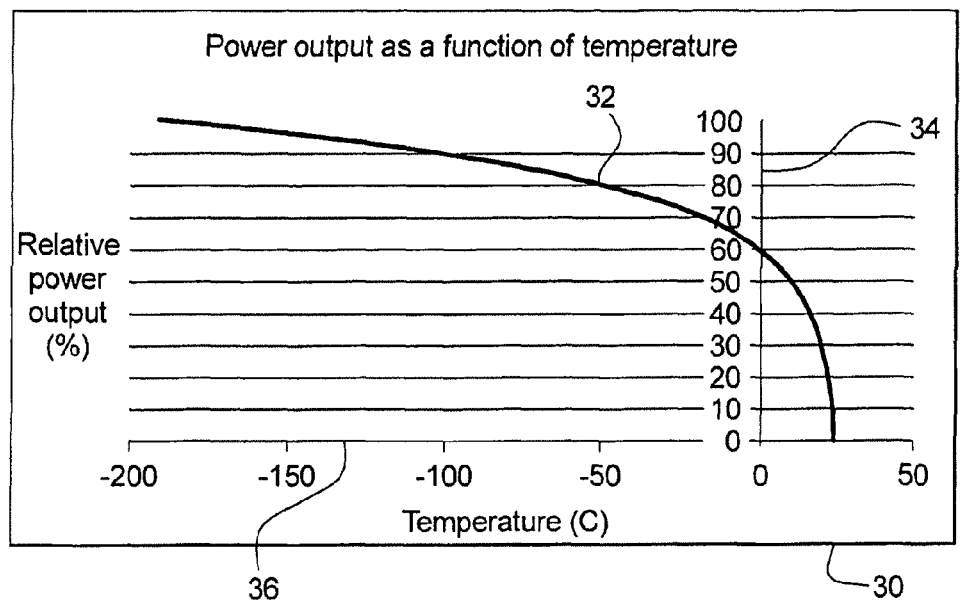
FIG. 1 is a graph of power output as a function of temperature for a thermoelectric device in the present stem cell delivery device.

A graph 30 in FIG. 1 shows the relative power output curve 32 of the TED 24 compared to the temperature of the pouch. In particular, the graph 30 shows the relative power output, on the vertical axis 34, of the thermoelectric device in the stem cell delivery device compared to the temperature, on the horizontal axis 36 generated by the device. Temperature is shown in Celsius and the power output is shown as a percent of possible power output by the heating element. The power output curve or profile can be varied depending upon the composition of the stem cell suspension in the pouch because different compositions of the suspension medium have different thermal conductivities.

When the stem cells in the pouch 20 have been thawed and are at a suitable temperature for injection then they are forced out of the pouch 20 by a suitable mechanical or pressure means. Means for squeezing the pouch may include pressurizing the delivery device with a disposable compressed gas cartridge or by providing rollers to squeeze the pouch, as shown in the following figures. Any means for pressing or squeezing the pouch or otherwise forcing the thawed cells from the cell container are encompassed within the scope of the present invention.

The advantages of the current invention over existing practices include that,

- ancillary equipment is not required to thaw out the stem cells;
- the stem cells do not have to be removed from the pouch and placed into a syringe after thawing;
- the stem cells are contained in their storage pouches up until they are injected into the thereby minimizing the risk of contamination of the stem cells.

Figure 2:
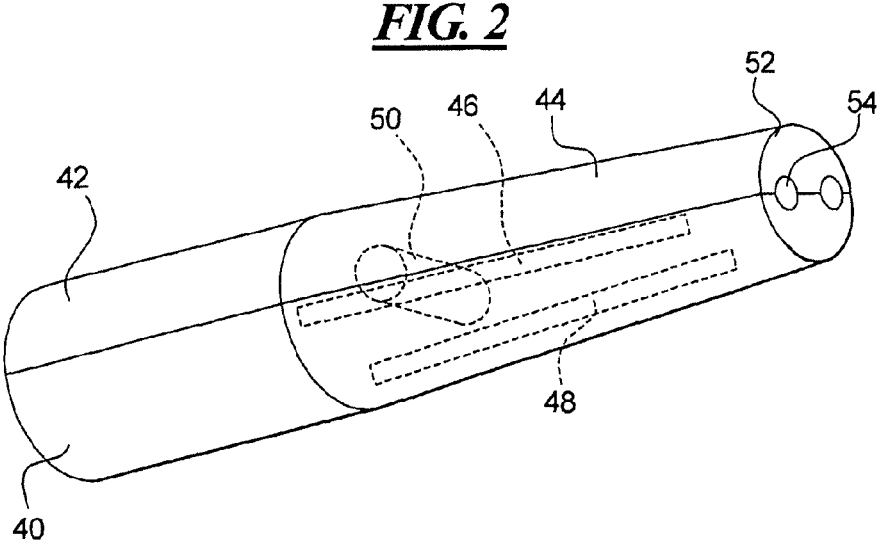
FIG. 2 is a sketch of the present device including descriptive text.

FIG. 2 shows an embodiment of the present stem cell delivery device 40. The delivery device includes a housing 42 within which is a compartment 44 into which is placed a pouch 46 containing frozen cells. The compartment 44 has a heating element 48 abutting the pouch 46 and a squeezing or pressure means 50 to exert pressure on the pouch 46 after thawing of the frozen cells. To operate the device 40, the pouch 46 containing the cryogenically frozen stem cells is inserted into the compartment 44 by opening a hinged top 52 of the device. The heating element 48 of a preferred embodiment is a Peltier thermoelectric device inside the delivery device that is in contact with the pouch 46 and that is operated to warm the pouch 46 and the cells therein. The squeezing apparatus 50 of the illustrated embodiment is a motor powered roller that is operable to squeeze the pouch 46 and thereby squeeze the stem cells out of the pouch. The stem cells are forced from the pouch 46 and down one or more tubes or needles that extend through openings 54 in the delivery device. After use, the pouch 46 is removed from the device 40 and the delivery device 40 kept for use again. The delivery device 40 need not be sterilizable since it does not contact the stem cells or body fluids. The delivery device 40 is reusable and may be used for sequential delivery of cells from a plurality of different pouches or for multiple sequential deliveries of cells from a single pouch.

A roller 50 is provided in the delivery device 40 to squeeze the pouch 46. The roller 50 may be mounted in the top section of the device or may be mounted in the lower section. The roller 50 is mounted adjacent the heating element 48. The front section 52 of the delivery device is connected to the housing 42 of the device by a hinge to permit pivoting movement of the front section 52 for opening to insert and/or remove the pouch 46 of stem cells. The front of the device 40 has two openings 54 to accommodate cell delivery tubes, which may be part of the pouch or may be selectively connected to the pouch and through which the cells are delivered to a patient or other cell receptor site.

The heating device 48 of a preferred embodiment is a Peltier device that is formed as a flat plate that is incorporated into the device below the roller 50. The roller 50 operates to squeeze the pouch 46 against the flat plate heating element. An external power source for the heating element and for the motor that drives the roller may be provided to keep the size of the device down, or a compact power source such as a battery may be provided within the delivery device. The motor for driving the roller may be linked to the roller by various drive means including gears, rollers, belts, or the roller may be directly driven by the motor. The delivery device may include more than one heater and may include various mechanical or pressurized delivery means positioned inside the device.

In FIG. 3, an embodiment of the stem cell delivery device 60 is shaped to fit comfortably into a user's hand. A rear section 62 provides an enclosure 64, such as for a roller motor and/or battery as well as control circuitry, and a front upper section 66 is hinged so that the top, front part of the device is selectively openable by a user. The front end 68 includes two openings 70 formed by the upper 66 and lower sections 72 of the front end for accommodating cell pouch tubes or needles. The illustration shows the top 74 and bottom 76 halves of the device 60 separated from one another, but in use the top 74 and bottom 76 are affixed together. The hinged front section 66 pivots at a hinge 67 an angle to the body of the device and is selectively fastenable into a closed position to enclose the pouch within a pouch compartment 78 and is releasable to permit opening for insertion and removal of the pouch in the compartment 78. Within the device is seen a roller 69 and the heating element 71.

FIG. 4 shows the side view of the device 60 with finger recesses 80 on the bottom surface of the lower part 76 and conical front end 82 of the bottom part. The top part 74 also has a conical front end 84, or more specifically a frustoconical end as both conical parts 82 and 84 end in a flat front face 68. A hinge pin 86 connects the back section 62 to the front portion 66 of the top 74 at the hinge 67.

Figure 5:
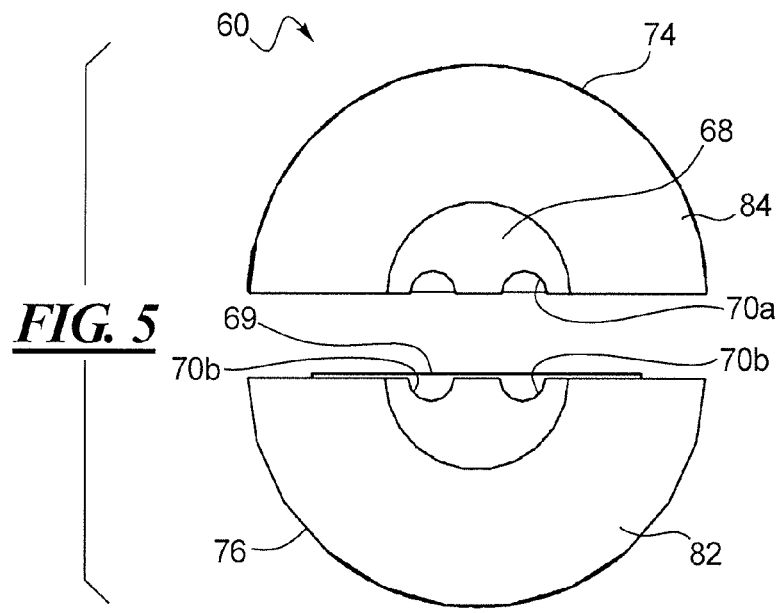
FIG. 5 is an end elevational view of the stem cell delivery device, shown with the two halves of the device separated.

Turning to FIG. 5, the front end of the device 60 has the flat front face 68 at the end of the conical sections 84 and 82 of the top and bottom parts, respectively. The two openings 70 for the stem cell pouch tubes or needles are formed by recesses 70a and 70b in the upper and lower portions of the conical end. The front end of the device 60 is generally circular in outline when viewed from the front when assembled, although the illustration of FIG. 5 shows the top and bottom parts 74 and 76 separated for purposes of illustration. The roller heating element 71 is visible in the lower part 76.

Figure 6:
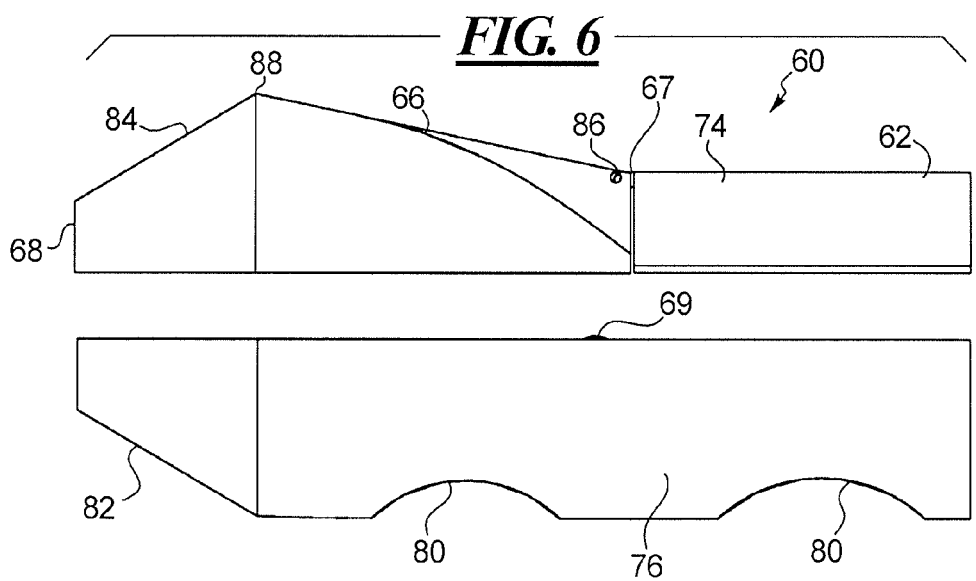
FIG. 6 is a side elevational view of the stem cell delivery device shown from the opposite site as compared to FIG. 4, shown with the two halves separated.

The side view of FIG. 6 of the device 60 is similar to the other side shown in FIG. 4, with the finger recesses 80 and the hinged top parts 66 and 62 connected by the hinge pin 86. In this view as well, the overall shape of the device 60 is seen, wherein the conical end 82 and 84 increases in diameter from the flat front end 68 to a ridge 88. From the ridge, the height of the lower part 76 is constant except for the finger recesses 80, whereas the top part 74 decreases in height from the ridge 88 to the hinge 67. From the hinge 67 rearward, the rear section 62 is of a constant height.

In FIG. 7, the top surface of the device 60 includes a flat grasping surface 90 that extends the length of the fixed rear portion 62 and from the hinge 67 to the beginning of the conical end 84 of the hinged front portion 66 at the ridge 88. The openings 86 through which the hinge pin has been inserted for the hinge 67 are shown. The grasping surface 90 provides the user with a surface to push against when connecting the device 60 to a tube or when pushing a needle into body tissues, for example.

In the back end view of FIG. 8, the top fixed portion 62 of the rear of the device 60 has the flat grasping surface 90 across a portion of the top thereof. The flat grasping surface 90 on the front top portion 66 ramps up to the full diameter of the generally cylindrical device at the ridge 88. The top part 74 has a flat end surface 92 and the bottom part 76 likewise has a flat end surface 94. The roller 69 is visible inside the device.

The unitary bottom part 76 is shown in the bottom view of FIG. 9, including the two finger recesses 80 and the conical front section 82. The finger recesses 80 form generally circular shapes into the cylindrical surface of the part 76. More or fewer recesses may be provided, or some other grip enhancing feature on the part may be used instead.

FIG. 10 shows the stem cell delivery device 60 in enlarged view. The separated top and bottom parts 74 and 76 permit a view into the interior 64, although as noted above the parts 74 and 76. The rear section 62 includes a space in the interior 64 for motors, batteries, electronic controls and other elements of the device. In the lower part 76 below the hinge 67 is the roller 69 mounted for sliding and rotating motion to exert a squeezing force on the pouch. Tracks 96 are provided in the device 60 along which the roller 69 slides during the pouch squeezing motion. The roller 69 may be driven by a motor in the space 64 that is powered by batteries or by an external power supply. The motor to drive the roller 69 may be mounted in the rear section, below the roller 69 or some other location. Between the roller 69 and the two tube or needle openings 70 at the conical end 82 and 84 is an interior space into which a pouch containing cryogenically frozen stem cells may be inserted by opening the hinged front portion 66. The pouch rests on the thermoelectric heating element 71 in the delivery device, either directly on the heating element 71 or on an overlying layer or covering. The cell pouch is squeezed between the roller 69 and the heating element 71. Rotation and/or sliding motion of the roller 69 draws the pouch into the nip between the roller 69 and the heating element 71, squeezing the contents of the pouch from the pouch opening(s), forcing the thawed cells out one or more tubes or needles connected at the pouch opening(s). The roller 69 may be provided with a covering or texture to prevent slipping on the pouch during squeezing.

FIG. 11 shows a somewhat more front view of the device 60 as compared to FIG. 10 wherein the planar or tablet shaped thermoelectric device 71 against which the frozen pouch is positioned is visible inside the hinged front section 66. The thermoelectric device 71 extends from at or near the conical front portion 82 to beneath the roller 69. The flat top surface of the thermoelectric device 71 permits the pouch to slide along the thermoelectric device and be drawn between the roller 69 and the back end of the thermoelectric device as the roller 69 is rotated. The pouch is drawn partially into the space 64 within the fixed rear portion 62 of the delivery device. Alternately, the roller 69 rides in tracks in the device over the pouch as the pouch remains stationary. The roller 69 may be disengaged from the squeezing position to release the pouch, or the roller may be reversed to permit removal of the pouch from the delivery device.

In FIG. 12, an alternate embodiment includes a single needle outlet for the thawed cells. The top part of the device 100 has been removed to reveal the interior of the lower part 102. In this embodiment, a single opening 104 is provided at the conical front end 106 where a needle 108 is attached to the pouch 110. The pouch 110 end opposite the needle 108 fits under the roller 112. The roller 112 is attached to two rails 114 and 116 and the rails in turn are connected to a motor 118. The motor 118 is powered by a rechargeable battery 120 in the back of the device 100. The battery 120 is recharged through leads 122 and 124 that connect to contact elements 126 and 128 mounted in the back end of the device 100. The contact pins 126 and 128 are contacted by contacts of a power source to charge the battery. The power source of a preferred embodiment is a base stand that is supplied with power through a transformer connecting to AC line power, for example. The base stand of a preferred embodiment is similar to charging stands provided for rechargeable portable telephones and the like.

The embodiment of FIG. 12 is also shown in FIG. 13 in cross sectional view. The front top portion 130 of the device 100 is shown in the open position and a pouch 110, also referenced 20, is inserted into the space at the front of the device 100. The needle 108 is connected to the pouch 20/110 extends from the device. The needle 108 is in a needle fitting 109 of the pouch. The pouch 20/110 rests on the thermo electrical heater device 24. Power is supplied to the heater device 24 from the battery 120 when an on/off switch 134 is moved to the "on" position. The frozen cells within the pouch 20/110 are thawed or defrosted. A control circuit may be provided for ensuring that the heating of the pouch is in accordance with a thawing temperature profile.

The on/off switch 134 also supplies battery power to the motor to activate the motor 118, which is connected to drive gear wheels 132 that engage the rails 114 and 116. The rails 114 and 116 move the roller forward over the pouch 20/110 to squeeze the cells from the pouch and out the needle 108. The motor 118 may be activated immediately, but preferably the operation of the motor is delayed until the cells in the pouch 20/110 are thawed sufficiently to delivery. A delay in the operation of the motor 118 may be controlled by feedback from the thermoelectric heating device, such as through use of a sensor circuit connected to between the heater and the motor. A timer may be used instead, or some other delay as well.

The delivery device 100 is provided with user controls, such as the switch 134 and possibly other controls as well as indicators for temperature, motor operation and other operating conditions. The controls and indicators may be provided either directly on the device or externally. For instance, the delivery device may have separate buttons or switches to provide user control of the heating function and squeezing function. Lights, indicators and/or display panels may be provided to indicate the operation of the heater and roller and may indicate the temperature of the pouch. A ready light may be provided. Control circuits for controlling the operation of the heater and roller and for the indicators and display are preferably included in the delivery device. The control circuit may be programmable to set a predetermined temperature profile for warming the cell pouch, and possibly for maintaining a predetermined temperature.

It is also contemplated that the heating of the pouch may commence on closing of the hinged part of the housing and thence the squeezing of the thawed cells commence upon detection of the desired delivery temperature. The control for this automatic operation may include a processor chip and associated circuitry. Control functions for the manually operated device may also include a processor controlling aspects of the heating and delivery. Sensors for detecting the presence of a pouch, the type of pouch, the type of material in the pouch, and other characteristics, may be provided.

The delivery device may be used for thawing a variety of frozen materials, including biological materials and body fluids, as well as non-biological materials.

Although other modifications and changes may be suggested by those skilled in the art, it is the intention of the inventors to embody within the patent warranted hereon all changes and modifications as reasonably and properly come within the scope of their contribution to the art.

I claim:

1. An apparatus for thawing and delivery of biological material, comprising:
   a housing defining an interior space;
   a thermoelectric heating element mounted in said interior space and having a heating surface configured to receive a biological material container;
   a squeezing apparatus mounted in said interior space and operable to exert a squeezing force on a biological material container received at the heating surface of said thermoelectric heating element; and
   a control for applying power to said thermoelectric heating element so as to warm biological material within the biological material container and to operate said squeezing apparatus so as to deliver the warmed biological material from the biological material container;
   wherein said squeezing apparatus is a roller pressing the biological material container against the thermoelectric heating device and operable to squeeze biological material from the container.

2. An apparatus for thawing and delivery of biological material, comprising:
   a housing defining an interior space, the housing defining a compartment within the housing, the housing being configured to enclose a container of biological material within the compartment when in a closed condition;
   a thermoelectric heating element mounted in said interior space and having a heating surface configured to receive a biological material container;
   a squeezing apparatus mounted in said interior space and operable to exert a squeezing force on a biological material container received at the heating surface of said thermoelectric heating element, the squeezing apparatus being operable to exert the squeezing force while the housing remains in the closed condition; and
   a control for applying power to said thermoelectric heating element so as to warm biological material within the biological material container and to operate said squeezing apparatus so as to deliver the warmed biological material from the biological material container;
   wherein said housing includes a first portion defining a fixed housing portion and a second portion having a selectively openable portion to provide access to the heating surface by a biological material container.

3. An apparatus for thawing and delivery of biological material, comprising:
   a housing defining an interior space, the housing defining a compartment within the housing, the housing being configured to enclose a container of biological material within the compartment when in a closed condition;
   a thermoelectric heating element mounted in said interior space and having a heating surface configured to receive a biological material container;
   a squeezing apparatus mounted in said interior space and operable to exert a squeezing force on a biological material container received at the heating surface of said thermoelectric heating element, the squeezing apparatus being operable to exert the squeezing force while the housing remains in the closed condition;
   a control for applying power to said thermoelectric heating element so as to warm biological material within the biological material container and to operate said squeezing apparatus so as to deliver the warmed biological material from the biological material container; and
   a rechargeable battery within the housing connected to supply power to at least one of said thermoelectric heating element and said squeezing apparatus.

4. An apparatus for thawing and delivery of biological material, comprising:
   a housing defining an interior space, the housing defining a compartment within the housing, the housing being configured to enclose a container of biological material within the compartment when in a closed condition;
   a thermoelectric heating element mounted in said interior space and having a heating surface configured to receive a biological material container;
   a squeezing apparatus mounted in said interior space and operable to exert a squeezing force on a biological material container received at the heating surface of said thermoelectric heating element, the squeezing apparatus being operable to exert the squeezing force while the housing remains in the closed condition;
   a control for applying power to said thermoelectric heating element so as to warm biological material within the biological material container and to operate said squeezing apparatus so as to deliver the warmed biological material from the biological material container; and
   a hand grip surface on an outside of the housing including finger notches formed into the housing, the housing being configured for holding in a user's hand.

5. An apparatus for thawing and delivery of biological material, comprising:
   a housing defining an interior space, the housing defining a compartment within the housing, the housing being configured to enclose a container of biological material within the compartment when in a closed condition;
   a thermoelectric heating element mounted in said interior space and having a heating surface configured to receive a biological material container;
   a squeezing apparatus mounted in said interior space and operable to exert a squeezing force on a biological material container received at the heating surface of said thermoelectric heating element, the squeezing apparatus being operable to exert the squeezing force while the housing remains in the closed condition;
   a control for applying power to said thermoelectric heating element so as to warm biological material within the biological material container and to operate said squeezing apparatus so as to deliver the warmed biological material from the biological material container; and
   contacts on said housing for receiving recharging power.

6. A method for delivering frozen biological materials, comprising the steps of:
   inserting a container of frozen biological materials into an enclosed compartment within a delivery device in thermal contact with a heating element;
   applying a heat to the container of frozen biological materials to thaw the biological materials;
   applying a squeezing force on the container while the container is in thermal contact with the heating element; and
   delivering thawed biological materials from the container while the container of biological materials remains within the enclosed compartment;
   wherein said step of inserting a container includes:
   pivotably opening a portion of a housing of a delivery device;
   inserting the container into the delivery device at the open portion; and
   pivotably closing the portion of the housing to enclose the container within the delivery device.

7. A method for delivering frozen biological materials, comprising the steps of:
inserting a container of frozen biological materials into a delivery device in thermal contact with a heating element;
applying a heat to the container of frozen biological materials to thaw the biological materials;
applying a squeezing force on the container while the container is in thermal contact with the heating element; and
delivering thawed biological materials from the container;
wherein said container is inserted into a handheld delivery device that encloses the container, the heating element, and the squeezing apparatus.

8. An apparatus for delivery of frozen biological material, comprising:
a housing having a conical first end and a second end, said conical first end defining a delivery opening;
a pivotably openable portion of the housing;

a thermoelectric heating element having a flat heating surface and mounted within an openable portion of the housing, the flat heating surface being configured to receive a pouch of frozen biological material and being operable to apply heat to the pouch;
a roller mounted within the housing and disposed to receive a pouch of frozen biological material between said roller and said heating element;
a motor operably connected to said roller and operable to rotate said roller so as to cause the roller to squeeze the pouch of biological material; and
a delivery conduit extending from said delivery opening of said conical first end of said housing through which the biological material is delivered upon application of squeezing force by the roller on the thawed biological material in the pouch.

* * * * *